(12) United States Patent
Boroczky et al.

(10) Patent No.: US 10,585,940 B2
(45) Date of Patent: Mar. 10, 2020

(54) METHOD AND SYSTEM FOR COMPUTER-AIDED PATIENT STRATIFICATION BASED ON CASE DIFFICULTY

(71) Applicant: KONINKLIJKE PHILIPS N.V., Eindhoven (NL)

(72) Inventors: Lilla Boroczky, Mount Kisco, NY (US); Michael Chun-Chieh Lee, Lexington, MA (US)

(73) Assignee: Koninklijke Philips N.V., Eindhoven (NL)

( * ) Notice: Subject to any disclaimer, the term of this patent is extended or adjusted under 35 U.S.C. 154(b) by 546 days.

(21) Appl. No.: 15/304,321

(22) PCT Filed: Apr. 16, 2015

(86) PCT No.: PCT/IB2015/052775
§ 371 (c)(1),
(2) Date: Oct. 14, 2016

(87) PCT Pub. No.: WO2015/173675
PCT Pub. Date: Nov. 19, 2015

(65) Prior Publication Data
US 2017/0061087 A1  Mar. 2, 2017

Related U.S. Application Data

(60) Provisional application No. 61/991,646, filed on May 12, 2014.

(51) Int. Cl.
*G06F 19/00* (2018.01)
*G06F 17/30* (2006.01)
(Continued)

(52) U.S. Cl.
CPC .... *G06F 16/5866* (2019.01); *G06F 16/24578* (2019.01); *G06F 19/321* (2013.01);
(Continued)

(58) Field of Classification Search
CPC .............. A61B 5/055; A61K 2039/505; A61K 2039/507; A61K 2039/545;
(Continued)

(56) References Cited

U.S. PATENT DOCUMENTS 5,319,543 A   6/1994 Wilhelm
5,839,438 A   11/1998 Graettinger et al.
(Continued)

FOREIGN PATENT DOCUMENTS

CN   1934589 A      3/2007
CN   102156715 A    8/2011
WO   2005096226 A2  10/2005

OTHER PUBLICATIONS

Jiao, et al., "Ultrasonic manifestations of uterine endometrial stromal sarcoma", Chin J Med Imaging Technol, 2014, vol. 30, No. 4, 3 pages (Absract).

*Primary Examiner* — Maroun P Kanaan

(57) ABSTRACT

When evaluating patient cases to determine complexity thereof, a computer-aided stratification technique is applied to analyze historical patient case diagnoses and correctness thereof in order to calculate a stratification score (20) for each of a plurality of abnormality types and/or anatomical locations. When a new patient case is received, the computer-aided stratification technique is applied to evaluate the patient case in view of historical data and assign a stratification score thereto. A ranked list (21) of current patient cases can be generated according to stratification scores, and physician workload can be adjusted as a function thereof so
(Continued)

that workload is balanced across physicians and/or according to physician experience level.

13 Claims, 3 Drawing Sheets

(51) Int. Cl.
G06F 16/58 (2019.01)
G06F 16/2457 (2019.01)
G16H 50/20 (2018.01)
G06Q 10/06 (2012.01)
G16H 50/70 (2018.01)
G16H 40/20 (2018.01)

(52) U.S. Cl.
CPC ... G06F 19/324 (2013.01); G06Q 10/063112 (2013.01); G16H 50/20 (2018.01); G16H 40/20 (2018.01); G16H 50/70 (2018.01)

(58) Field of Classification Search
CPC ............ A61K 2039/55; C07K 2317/24; C07K 2317/565; G16H 50/30; G16H 10/60; G16H 50/20; G16H 50/70; G06Q 10/06
See application file for complete search history.

(56) References Cited

U.S. PATENT DOCUMENTS

| | | | |
|---|---|---|---|
| 7,640,051 | B2 | 12/2009 | Krishnan et al. |
| 8,560,341 | B2 | 10/2013 | Iwase et al. |
| 9,111,027 | B2 | 8/2015 | Kozuka et al. |
| 9,133,959 | B2 | 9/2015 | Minervini |
| 9,477,809 | B2 | 10/2016 | Marx |
| 2004/0141639 | A1 | 7/2004 | Matsui |
| 2005/0020903 | A1 | 1/2005 | Krishnan et al. |
| 2009/0082637 | A1* | 3/2009 | Galperin ............... G06F 19/321 600/300 |
| 2010/0280842 | A1 | 11/2010 | Iwase et al. |
| 2012/0095331 | A1 | 4/2012 | Chashi |
| 2012/0253836 | A1 | 10/2012 | Nolte et al. |
| 2014/0039852 | A1 | 2/2014 | Zhang |

* cited by examiner

METHOD AND SYSTEM FOR COMPUTER-AIDED PATIENT STRATIFICATION BASED ON CASE DIFFICULTY

CROSS-REFERENCE TO PRIOR APPLICATIONS

This application is the U.S. National Phase application 35 U.S.C.§ 371 of International Application No. PCT/IB2015/052775, filed on Apr. 16, 2015, which claims the benefit of U.S. Provisional Application No. 61/991,646, filed on May 12, 2014. These applications are hereby incorporated by reference herein.

The present innovation finds application in medical diagnosis technologies, particularly with regard to computer-aided diagnosis therein. However, it will be appreciated that the described techniques may also find application in other patient diagnosis systems, other diagnosis scenarios, other stratification techniques, and the like.

Accurate diagnosis is important for disease management and therapy of a patient. To arrive at an accurate diagnosis, physicians often spend a long time reading, studying, and creating recommendations for "difficult" cases, i.e. unusual or complex cases. On the other hand, for easier diagnosis cases the physician's diagnosis and recommendations for the next steps can be generated in a very short time. This is especially true for junior physicians, as if they are presented with a difficult case they often need to request a second opinion of a more senior colleague. That is, there can be a significant difference in the amount of time and effort involved for a physician to assess a difficult case versus an easy case. An example of this is where a radiologist is asked to assess an image where a lesion is clearly visible and clearly malignant versus a case where the lesion is difficult to see and has a mix of malignant and benign characteristics.

In hospital radiology practice, the radiologist typically works through a daily worklist stored in a radiology information system (RIS) or picture archiving and communication system (PACS) and consisting of recently imaged patients. These systems typically do not consider the "difficulty" of a case, but rather the patients are sorted based on types of exams only, without the notion that a particular case may be difficult to diagnose or not. Conventional systems may have only the intelligence to sort and present the cases by imaging modality and specialty. For example they can sort the cases based on organs (e.g. breast, liver, etc.) and/or imaging modality (CT, X-ray, ultrasound, DCE-MRI, etc.) only.

The present application provides new and improved systems and methods that facilitate stratifying patient cases according to potential diagnosis difficulty level, which overcome the above-referenced problems and others.

In accordance with one aspect, a method of ranking patient cases according to difficulty level comprises, for each of a plurality of patient cases: retrieving from a database an image study for a patient; identifying an abnormality in a patient image included in the image study; analyzing patient demographic and clinical information; and calculating a computer-aided stratification score for the patient case as a function of the identified abnormality and the patient demographic and clinical information; The method further comprises outputting a ranked list of the patient cases according to the respective stratification score assigned to each patient case.

According to another aspect, a system that facilitates ranking patient cases according to difficulty level comprises a computer-aided stratification module comprising a processor adapted to, for each of a plurality of patient cases: retrieve from a database an image study for a patient; identify an abnormality in a patient image included in the image study; analyze patient demographic and clinical information; and calculate a computer-aided stratification score for the patient case as a function of the identified abnormality and the patient demographic and clinical information. The processor is further configured to output (e.g., to a user interface, a printer, or the like) a ranked list of the patient cases according to the respective stratification score assigned to each patient case.

According to another aspect, a computer-readable medium has stored thereon computer-executable instructions for ranking patient cases according to difficulty level, the instructions comprising, for each of a plurality of patient cases: retrieving from a database an image study for a patient; identifying an abnormality in a patient image included in the image study; analyzing patient demographic and clinical information; and calculating and assigning a computer-aided stratification score for the patient case as a function of the identity of the abnormality and the patient demographic and clinical information. The instructions further comprise outputting a ranked list of the patient cases according to the respective stratification score assigned to each patient case.

One advantage is that physician workload balance is improved.

Another advantage is that difficult diagnoses can be identified for additional scrutiny.

Still further advantages of the subject innovation will be appreciated by those of ordinary skill in the art upon reading and understand the following detailed description.

The drawings are only for purposes of illustrating various aspects and are not to be construed as limiting.

Figure 3:
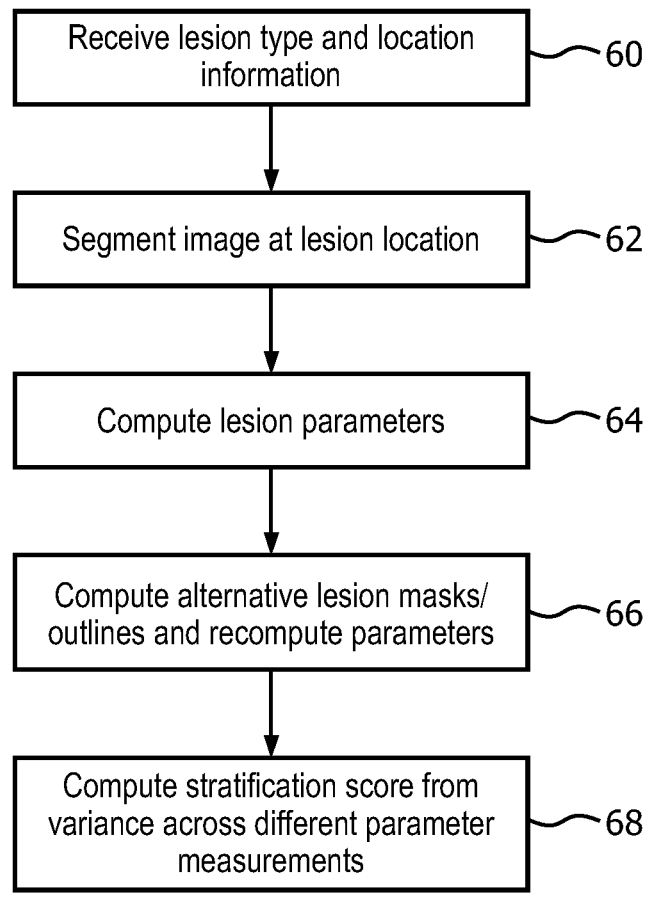
Figure 4:
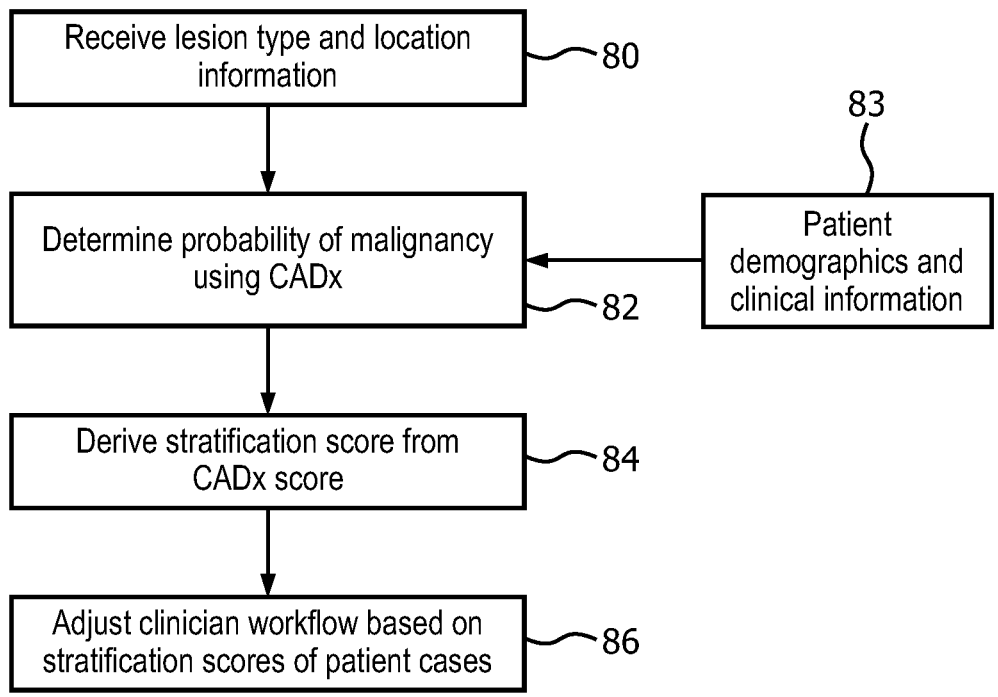

FIG. 3 illustrates a method for performing computer-aided stratification of diagnosis difficulty level for a plurality of patient cases as a function of lesion parameter analysis, in accordance with one or more aspects described herein FIG. 4 illustrates a method for performing computer-aided stratification of diagnosis difficulty level for a plurality of patient cases using computer-aided diagnosis (CADx), in accordance with one or more aspects described herein.

Figure 5:
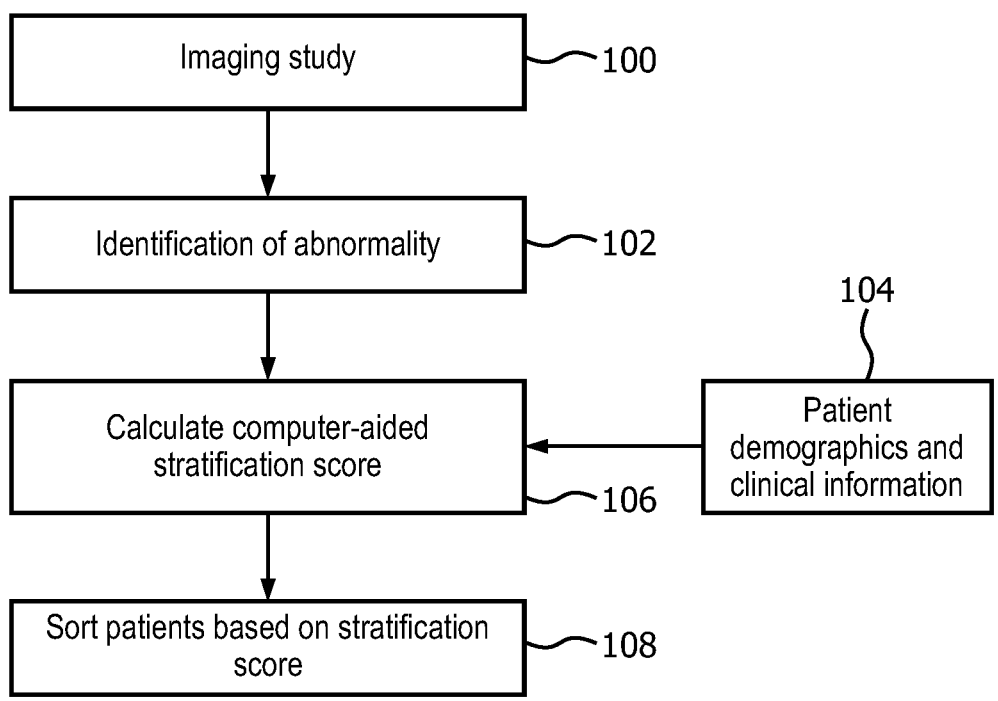

FIG. 5 illustrates a method for performing computer-aided stratification of diagnosis difficulty level for a plurality of patient cases, in accordance with one or more aspects described herein.

The described systems and methods overcome the above-mentioned problems by stratifying patient cases according to a level of difficulty associated with the diagnoses of the patients. For instance, to maximize efficiency and accuracy, the assignment of cases to physician worklists includes difficulty as a factor. For example, easier cases can be assigned to junior physicians, while more complex cases are reserved for more senior personnel. In another example, a mix of cases may be equally distributed across different physicians. The current innovation thus facilitates assessing the difficulty of a case and employing the result of the assessment to adjust a clinical workflow. For instance, patient cases are assigned to a particular physician not only based on organ type or imaging modality, but also based on diagnosis difficulty level. In another embodiment, an alert is generated if a case is determined to be highly complex, such as an alert that recommends a second physician's review and/or whether the case would be a useful teaching case.

Figure 1:
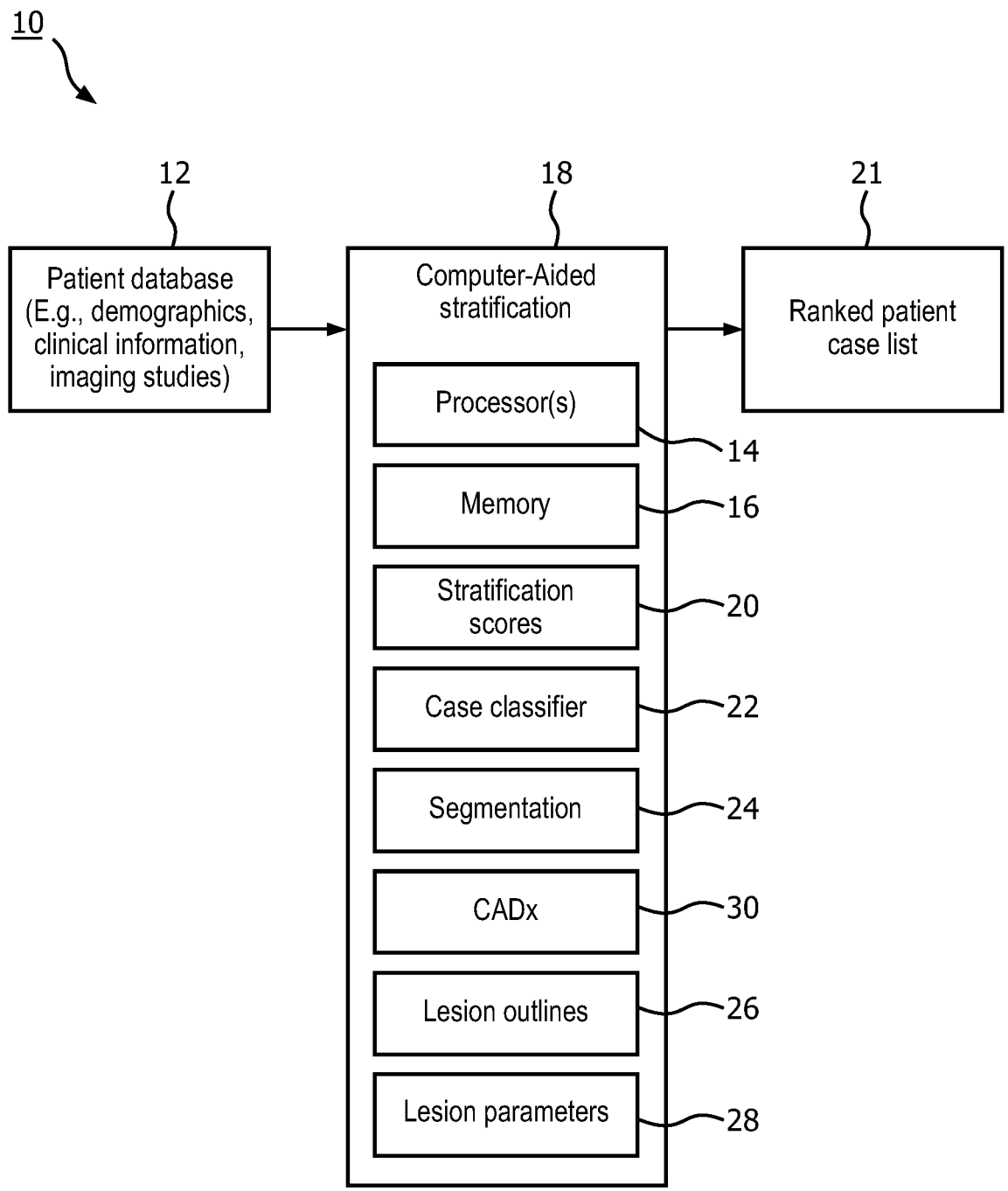
FIG. 1 illustrates a system that facilitates performing computer-aided patient stratification to sort patients according to case difficulty, in accordance with one or more aspects described herein.

FIG. 1 illustrates a system 10 that facilitates performing computer-aided patient stratification to sort patients according to case difficulty, in accordance with one or more aspects described herein. The system takes as its input a current patient's clinical case that is to be evaluated for a specific clinical question. The clinical case can include patient information or data comprising patient demographic information, clinical information, a current imaging study, etc. A database 12 stores patient information, including but not limited to demographic information, e.g. gender, age, ethnicity, etc. The database also stores clinical information for each of a plurality of patients, which may include, e.g. family history, medical history, reason for the imaging study, current condition, symptoms, current treatments, risk factors, etc. Also stored in the database are acquired imaging studies for one or more patients, including, e.g. a CT scan, an MM scan, a PET scan, a SPECT scan, an ultrasound scan, an x-ray or the like.

The clinical question may be broadly described as a screening task (e.g., detection of abnormalities, or the like), a diagnosis task (e.g., characterization of abnormalities as to their nature and/or malignancy), or an evaluation task (e.g., measurements, assessment of disease progression and/or treatment efficacy). The question may be narrowed further by specifying location(s) in the image for evaluation, such as an organ in which abnormalities are being search (e.g. search for breast lesions) or a specific tumor that is being assessed. This information can be included in the metadata associated with the patient or image information (such as in a private DICOM field or as a computer-interpretable segment of a clinical note).

The system further comprises a processor 14 that executes, and a memory 16 stores, computer-executable instructions for performing the various functions, methods, techniques, applications, etc., described herein. The memory 16 may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor 14 can read and execute. In this context, the system 10 may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphics processing unit (GPU), or PAL, or the like.

A computer-aided stratification (CAS) module 18 is executed on the clinical case data 12 to generate a stratification score 20. The score may be numerical (such as 0-100) or categorical (such as "easy", "moderate", and "difficult"). In one embodiment the CAS module uses the imaging data to generate the stratification score. In other embodiment the CAS module also uses the demographics and other non-imaging information, as is described above. The computer-aided stratification module 18 generates the stratification score, which is used to sort the patient case based on the predicted difficulty of the case with respect to the clinical question. In another embodiment, the CAS module 18 computes a stratification score that assesses the difficulty in characterizing a given lesion.

The CAS module 18 outputs a ranked patient list 21, which can be ranked according to the stratification scores (e.g., level of diagnosis difficulty) associated with respective patient cases. The patient list can also include, e.g., alerts recommending a second physician's review (e.g., a second opinion) for specified patient cases, alerts recommending that a particular case be used as a teaching case or the like, etc. The stratification scores or ranking for each patient case can be used, e.g., to ensure that difficult cases are assigned to senior physicians, to ensure that an excessive number of difficult cases is not assigned to any one physician (to balance workload across physicians), etc.

Figure 2:
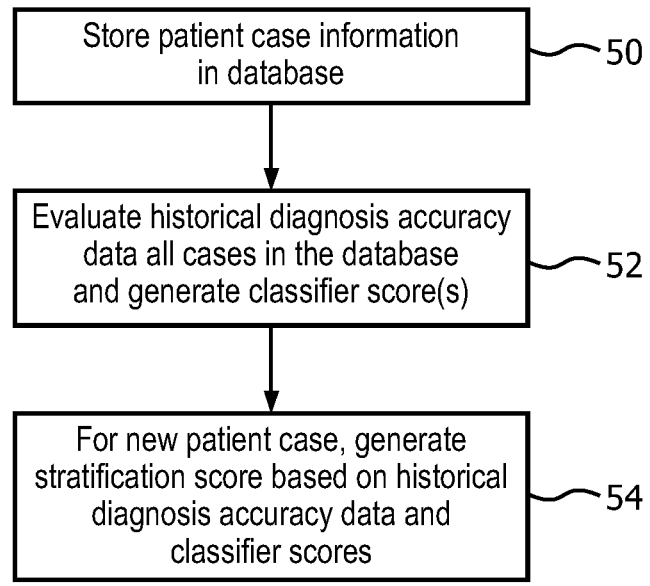
FIG. 2 illustrates a method for performing computer-aided stratification of diagnosis difficulty level for a plurality of patient cases using historical diagnosis accuracy data, in accordance with one or more aspects described herein.

With continued reference to FIG. 1, FIG. 2 illustrates a method for performing computer-aided stratification of diagnosis difficulty level for a plurality of patient cases, in accordance with one or more aspects described herein. At 50, a database is collected (e.g., a priori) comprising, e.g., patient demographic information, clinical information, imaging study information, etc., and over a large number of cases. The database also includes the diagnostic assessment of a reading (diagnosing) radiologist, e.g. regarding whether the specified lesion is malignant or benign. The database further comprises the actual diagnosis as determined by pathology or other adjunct measures, such as stability over time (suggestive of benign processes). Thus, the database includes data indicative of both the radiologist assessment and whether or not the radiologist's assessment was correct. At 52, using machine learning techniques, a computer classifier 22 performs a mathematical transformation that renders the data in the database into a numerical measure of determine likelihood that the physician's diagnostic assessment (e.g., whether a tumor is malignant or benign) will match the truth (i.e., the actual correct diagnosis as determined by pathology or the like). That is, CAS module predicts whether a radiologist is likely to assess the case correctly or incorrectly. In one example, historical diagnosis accuracy over a number of patient cases is used to assign stratification scores to current patient cases. For instance, the CAS module determines whether a particular type of lesion is misdiagnosed at a rate above a predetermined threshold, and assigns that particular type of lesion a "difficult" rating or score. To further this example, a radiologist may regularly determine that a particular tumor or tumor location is malignant and order a biopsy procedure. If the biopsy regularly indicates that the tumor is benign, the particular tumor type or location (or other tumor metric) can be associated with a stratification score of "difficult". It will be appreciated that the foregoing example is not limited to misdiagnoses as a metric for assigning the stratification score, but rather other metrics may be employed, such as characteristics of the images or the computed metrics describing the level of uncertainty expressed in radiology reports. At 54, when applied to a new case for which the specific lesion location (or type or other metric) is pre-specified, as previously described, the score generated by the classifier becomes the stratification score. In one embodiment, the CAS algorithm can provide a stratification score for each individual radiologist based on the diagnostic accuracy of the particular physician.

With continued reference to FIG. 1, FIG. 3 illustrates a method for performing computer-aided stratification of diagnosis difficulty level for a plurality of patient cases, in accordance with one or more aspects described herein. For instance, the CAS module 18 computes the stratification score that assesses the difficulty in measuring a given lesion. In a case where the specific lesion to be measured is pre-specified, the location of the lesion is taken as an input parameter, at 60. A segmentation algorithm 24 for segmenting a lesion on an image is executed by the processor on the specified lesion location, at 62. This produces a lesion outline or mask 26 which can be used to compute lesion parameters 28 such as surface area, volume, long-axis, short-axis, or similar common clinical measurements, at 64. A plurality of alternative lesion outlines (and consequently, alternative masks) can be computed, at 66, for example as follows. The input location may be perturbed, for example, by randomly sampling from a neighborhood with a set distribution, such as 1 or 2 mm standard deviation. Alternatively, a plurality of different segmentation algorithms may be run with the same input, again resulting in a variety of measurements. At 68, the stratification score is derived directly from the variance across the different measurements. The stratification score indicates an estimate of how different radiologists or algorithms would differ in their assessment of the particular lesion. For example, if a small change to one or more input parameters results in a large change in the segmentation results, then the case can be assigned a "difficult" stratification score. On the other hand, if large variances in input values result in minimal differences in output values, then the case can be assigned an "easy" stratification score. In one embodiment, the actual radiologist workflow may be entirely manual. In another embodiment, the automated segmentation is employed to estimate the uncertainty and compute the stratification score.

With continued reference to FIG. 1, FIG. 4 illustrates a method for performing computer-aided stratification of diagnosis difficulty level for a plurality of patient cases, in accordance with one or more aspects described herein. The CAS module 18 computes the stratification score that assesses the difficulty in characterizing a given lesion. At 80, the specific lesion to be characterized is pre-specified, and the location of the lesion is taken as an input parameter. A computer-aided diagnosis (CADx) algorithm 30 is executed by the processor to compute the probability of malignancy of the lesion based on image information, at 82. In another embodiment, the CADx algorithm can use image information and patient demographic and clinical information provided at 83, when determining the probability of malignancy of the lesion at 82. Techniques for CADx may include, e.g., those that produce scores between 0-100, with 100 denoting the highest probability of malignancy. At 84, a stratification score can then be derived based directly on the CADx score. A very high (or very low) CADx score (e.g. <20 or >80) can correspond to "easy" cases. "Moderate" and "difficult" cases can similarly be mapped.

The CAS module stratification score output is used to affect the workflow of case reading by clinicians in various manners, at 86. For instance, the cases can be further sorted and assigned to the physicians based on the physicians' experience. For example, the most difficult cases can be assigned to senior physicians with a certain number of years of experience, while the moderately difficult cases are assigned to the less-experienced physicians. In another embodiment, cases can be sorted and assigned to physicians in order to reduce the variation in difficulty-level across physicians, i.e. for each physician, defining a workload metric by computing the sum of the stratification scores over all of the given physician's cases for the day, and then selecting a distribution that minimizes the cross-physician variance in this workload metric.

In another embodiment, cases can be sorted within a single physician's worklist in order to distribute difficult cases evenly across the day, for example, by again defining a workload metric and then selecting a distribution that minimizes the hour-to-hour (or other time scale) variance in this workload metric for a single physician. In another embodiment, an indicator can be placed next to patients within a worklist (e.g. on a RIS), indicating the complexity of each patient's case. The indicator may be a flag based on a threshold, i.e. for cases above a certain level of complexity, or a numerical value, or a visual indicator such as a color flag, graphical line, or the like indicative of that value.

According to another example, exceptionally difficult cases can be flagged for automatic double reading, i.e. reading by a second radiologist. This can be implemented by setting a threshold that exceeds a threshold above which this event is triggered. In another embodiment, difficult cases can be flagged for possible inclusion in a teaching file or as a case study.

FIG. 5 illustrates a method for performing computer-aided stratification of diagnosis difficulty level for a plurality of patient cases, in accordance with one or more aspects described herein. At 100, an imaging study is generated or retrieved from a database of a particular patient. The imaging study may be of any suitable imaging modality, such as MM, CT, ultrasound, x-ray, nuclear, etc. At 102, an abnormality (e.g., a lesion) is identified. In one embodiment, the abnormality is identified using computer-aided detection. In another embodiment, the abnormality is manually annotated or identified. At 104, patient demographic information and/or clinical information are retrieved. At 106, a computer-aided stratification score is calculated as a function of the patient demographic information, the clinical information and the lesion identity, or any combination of the foregoing information. That is, the score can be calculated using CADx, based on image segmentation data, or the like. Acts 100, 102, 104, and 106 are iteratively performed for each of a plurality of patient cases. At 108, patient cases are sorted according to their stratification scores.

According to an example, a breast dynamic contrast enhanced (DCE)-magnetic resonance imaging (MRI) screening study is performed on a 43-year old woman. The patient's family history includes a mother who died at age 45 due to breast cancer. As soon as the DCE-MRI study is available in the hospital PACS system, the CAS algorithm is run on the case in the background. A computer-aided detection algorithm identifies a breast lesion at the left breast of the patient. Then, a computer-aided diagnosis (CADx) algorithm is executed to derive a likelihood score (e.g., between 0 and 100) for malignancy, where the higher likelihood scores correspond to a greater probability of malignancy. If the likelihood score is, e.g., between 0 and 20 or between 80 and 100, the stratification score is "easy"; if the score between 20-30 or 70-80 the stratification score is "moderate", and the score is "difficult" if the CADx algorithm output is 30-70. Both computer-aided detection and computer-aided diagnosis algorithms can be employed (e.g., by performing segmentation of the lesion, feature extraction based the image and segmentation boundary, and a classifier to calculate a likelihood score).

To further this example, the CAS algorithm also uses demographics and other non-image-based information related to the patients. For example, in the above example, the woman has a family history of breast cancer, so even though the stratification score is "easy", the score might be elevated to be "moderate" due to this extra clinical information, which in turn may cause the case to be assigned to more experienced physicians or double-read as a consequence.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A method of ranking patient cases according to diagnosis difficulty level, comprising, for each of a plurality of patient cases:
   retrieving, from a database, an image study for a patient;
   identifying an abnormality in a patient image included in the image study;
   analyzing patient demographic and clinical information;
   calculating a computer-aided stratification score for the patient case as a function of the identified abnormality and the patient demographic and clinical information;
   outputting a ranked list of the patient cases according to the respective stratification score assigned to each patient case; wherein the method further comprises:
     storing a plurality of patient cases that were previously diagnosed by a first physician in the database;
     evaluating historical diagnosis accuracy for the plurality of previously-diagnosed patient cases;
     using machine learning techniques to generate an accuracy score indicative of diagnosis accuracy for each of a plurality of types of patient cases;
     receiving information describing a current patient case type;
     calculating a final stratification score for the current patient case based on the type of the current patient case and the accuracy score for the type of the current patient case; and
     generating an alert after the final stratification score exceeds a threshold, wherein the alert recommends review by a second physician.

2. The method according to claim 1, further comprising, for each patient case:
   receiving lesion type and location information for a lesion in the patient image;
   segmenting the image at a location of the lesion to generate a first lesion outline;
   computing one or more lesion parameters from the first lesion outline;
   computing one or more alternative lesion outlines;
   computing one or more lesion parameters from the one or more alternative lesion outlines; and
   computing the stratification score as a function of lesion parameter variances between the lesion outline and the one or more alternative lesion outlines.

3. The method according to claim 2, wherein the computing of one or more alternative lesion outlines further comprises one of:
   randomly sampling image data from a neighborhood with a set distribution about the lesion location; and
   employing a plurality of different segmentation algorithms to segment the image at the lesion location.

4. The method according to claim 2, wherein the lesion parameters comprise one or more of lesion surface area, lesion volume, a long axis of the lesion, and a short axis of the lesion.

5. The method according to claim 1, further comprising, for each patient case:
   receiving lesion type and location information for a lesion in the patient image;
   executing a computer-aided diagnostic (CADx) technique on one or more of the lesion in the patient image, and patient demographic and clinical information;
   determining a probability of malignancy of the lesion;
   deriving the stratification score for the patient case from the probability of malignancy; and
   adjusting a clinician workflow as a function of stratification scores for of the plurality of patient cases.

6. The method according to claim 1, further comprising:
   flagging at least one patient case, as a function of the stratification score for the at least one patient case, as being a candidate for academic use as a teaching case.

7. A system that facilitates ranking patient cases according to diagnosis difficulty level, comprising:
   a computer-aided stratification module comprising a processor adapted to, for each of a plurality of patient cases:
   retrieve from a database an image study for a patient;
   identify an abnormality in a patient image included in the image study;
   analyze patient demographic and clinical information;
   calculate a computer-aided stratification score for the patient case as a function of the identified abnormality and the patient demographic and clinical information; and
   output a ranked list of the patient cases according to the respective stratification score assigned to each patient case wherein the system further comprises:
   a non-transitory computer readable medium that stores a plurality patient cases that were previously diagnosed by a first physician; and wherein the processor is further configured to:
   evaluate historical diagnosis accuracy for the plurality of previously-diagnosed patient cases:
   using machine learning techniques to generate an accuracy score indicative of the diagnosis accuracy for each of a plurality of types of patient cases;
   receive information describing a current patient case type;
   calculate a final stratification score for the current patient case based on the type of the current patient case and the accuracy score for the type of current patient case; and
   generating an alert after the final stratification score exceeds a threshold, wherein the alert recommends review by a second physician.

8. The system according to claim 7, wherein the abnormality is a lesion and the stratification score is calculated at least in part by segmenting an image of the lesion.

9. The system according to claim 7, wherein the processor is further configured to, for each patient case:
   receive lesion type and location information for a lesion in the patient image;
   segment the image at a location of the lesion to generate a first lesion outline;
   compute one or more lesion parameters from the first lesion outline;
   compute one or more alternative lesion outlines;
   compute one or more lesion parameters from the one or more alternative lesion outlines; and
   compute the stratification score as a function of lesion parameter variances between the lesion outline and the one or more alternative lesion outlines.

10. The system according to claim 9, wherein computing the one or more alternative lesion outlines further comprises one of:
   randomly sampling image data from a neighborhood with a set distribution about the lesion location; and
   employing a plurality of different segmentation algorithms to segment the image at the lesion location.

11. The system according to claim 9, wherein the lesion parameters comprise one or more of lesion surface area, lesion volume, a long axis of the lesion, and a short axis of the lesion.

12. The system according to claim 7, wherein the processor is further configured to, for each patient case:
   receive lesion type and location information for a lesion in the patient image;
   execute a computer-aided diagnostic (CADx) technique on one or more of the lesion in the patient image, and patient demographic and clinical information;
   determine a probability of malignancy of the lesion;
   derive the stratification score for the patient case from the probability of malignancy; and
   adjust a clinician workflow as a function of stratification scores for of the plurality of patient cases.

13. A non-transitory computer-readable medium having stored thereon computer-executable instructions for ranking patient cases according to diagnosis difficulty level, the instructions comprising, for each of a plurality of patient cases:
   retrieving from a database an image study for a patient;
   identifying an abnormality in a patient image included in the image study; analyzing patient demographic and clinical information;
   calculating and assigning a computer-aided stratification score for the patient case as a function of the identity of the abnormality and the patient demographic and clinical information; and
   outputting a ranked list of the patient cases according to the respective stratification score assigned to each patient case wherein the instructions further comprise:
   storing a plurality of patient cases that were previously diagnosed by a first physician in the database;
   evaluating historical diagnosis accuracy for the plurality of previously-diagnosed patient cases;
   using machine learning techniques to generate an accuracy score indicative of the diagnosis accuracy for each of a plurality of types of patient cases;
   receiving information describing a current patient case type; and
   calculating a final stratification score for the current patient case based on the type of the current patient case and the accuracy score for the type of the current patient case, and
   generating an alert after the final stratification score exceeds a threshold, wherein the alert recommends review by a second physician.

* * * * *